(12) United States Patent
Stroud, Jr.

(10) Patent No.: US 10,675,209 B1
(45) Date of Patent: Jun. 9, 2020

(54) FLUID THERAPY DEVICE

(71) Applicant: Samuel J. Stroud, Jr., Durham, NC (US)

(72) Inventor: Samuel J. Stroud, Jr., Durham, NC (US)

(73) Assignee: Karen Guthrie Stroud, Durham, NC (US)

( * ) Notice: Subject to any disclaimer, the term of this patent is extended or adjusted under 35 U.S.C. 154(b) by 942 days.

(21) Appl. No.: 15/259,162

(22) Filed: Sep. 8, 2016

(51) Int. Cl.
*A61F 7/00* (2006.01)
*A61H 9/00* (2006.01)
*A61H 1/00* (2006.01)

(52) U.S. Cl.
CPC ......... *A61H 9/0071* (2013.01); *A61F 7/0085* (2013.01); *A61H 1/008* (2013.01); *A61H 9/0057* (2013.01); *A61F 2007/0064* (2013.01)

(58) Field of Classification Search
CPC .... A61H 9/0071; A61H 1/008; A61H 9/0057; A61H 7/007; A61H 7/008; A61H 9/00; A61H 9/005; A61H 2201/12; A61H 2201/1207; A61H 2201/164; A61H 2201/1642; A61H 2201/50; A61H 2201/5007; A61H 2201/5056; A61H 2205/12; A61H 2205/125; A61F 7/0085; A61F 2007/0064
USPC ........................................ 601/6, 7, 9, 10, 11
See application file for complete search history.

(56) References Cited

U.S. PATENT DOCUMENTS

| | | | |
|---|---|---|---|
| 2,720,041 A | 10/1955 | Kajtar | |
| 3,050,875 A | 8/1962 | Robbins | |
| 4,428,368 A * | 1/1984 | Torii | A61H 9/005 |
| | | | 601/15 |
| 4,468,869 A | 9/1984 | Fukuoka | |
| 5,584,130 A | 12/1996 | Perron | |
| 5,815,949 A | 10/1998 | Sessa | |
| 6,729,044 B2 | 5/2004 | Vello | |
| 7,540,848 B2 | 6/2009 | Hannigan et al. | |
| 7,618,382 B2 | 11/2009 | Vogel et al. | |
| 8,052,624 B2 | 11/2011 | Buchanan et al. | |
| 8,313,449 B2 | 11/2012 | Hardman et al. | |
| 8,388,562 B2 | 3/2013 | Baker et al. | |
| 8,460,355 B2 | 6/2013 | Cazzini et al. | |
| 2002/0133106 A1 * | 9/2002 | Peled | A43B 7/00 |
| | | | 601/149 |
| 2006/0141180 A1 | 6/2006 | Park | |
| 2007/0256333 A1 | 11/2007 | Wolf, Jr. | |

(Continued)

*Primary Examiner* — Quang D Thanh
(74) *Attorney, Agent, or Firm* — Tuggle Duggins P.A.; Blake P. Hurt

(57) ABSTRACT

A high-velocity fluid therapy device including a negative-pressure source positioned within a housing with a pair of opposingly oriented sidewalls connected by a laterally extending dowel. The negative-pressure source is in fluid communication with one or more treatment platforms, each platform having one or more longitudinally oriented fluid channels and one or more laterally oriented fluid channels. The channels and conduits permit the airflow pulled by the negative-pressure source to pass over the treatment surface, into the channels and conduits, and eventually internalized by the fluid therapy device to reduce the surface temperature of the treatment area, reducing swelling and inflammation, resulting in reduced pain experienced at the treatment site.

15 Claims, 3 Drawing Sheets

(56) References Cited

U.S. PATENT DOCUMENTS

| | | | |
|---|---|---|---|
| 2008/0021531 A1* | 1/2008 | Kane | A61F 7/02 |
| | | | 607/111 |
| 2008/0097263 A1 | 4/2008 | Grigoriev et al. | |
| 2009/0113767 A1 | 5/2009 | Lee | |
| 2009/0234259 A1* | 9/2009 | Hardman | A43B 3/0005 |
| | | | 601/134 |
| 2010/0106230 A1* | 4/2010 | Buchanan | A61F 7/00 |
| | | | 607/111 |
| 2010/0210983 A1* | 8/2010 | Baker | A43B 7/1445 |
| | | | 601/152 |
| 2014/0088476 A1 | 3/2014 | Logan et al. | |

* cited by examiner

FLUID THERAPY DEVICE

FIELD OF THE INVENTION

The invention herein pertains to relief systems generally and particularly pertains to a manifold system for applying fluid stimulus to the exterior surface of the foot, back, or other body part needing treatment.

DESCRIPTION OF THE PRIOR ART AND OBJECTIVES OF THE INVENTION

Clinical studies and practice have shown that providing a reduced pressure in proximity to a tissue site augments and accelerates the growth of new tissue at the tissue site. The applications of this phenomenon are numerous, but application of reduced pressure has been particularly successful in treating inflammation and wounds. This treatment (frequently referred to in the medical community as "negative pressure wound therapy," "reduced pressure therapy," or "vacuum therapy") provides a number of benefits, which may include faster healing and increased formulation of granulation tissue. For an example of this type of system, see U.S. Pat. No. 8,313,449 to Hardman et al., entitled Foot Manifolds, Apparatuses, Systems, and Methods for Applying Reduced Pressure to a Tissue Site on a Foot.

While the prior art includes solutions for medical treatment relying on vacuum methods (as described above), these systems are not without their flaws. By definition, the vacuum system is only as effective as the system which defines it, as a vacuum is an enclosed space from which matter, especially air, has been partially removed so that the matter or gas remaining in the space exerts less pressure than the atmosphere. Even in the clinical setting, but more so in the residential setting, the repeated use of a device relying on such a system is bound to experience loss of operant functionality over time. Other issues such as system complexity, cost, and user error further illustrate why the known solutions to pain relief and inflammation, particularly in view of vacuum systems, are deficient.

Thus, in view of the problems and disadvantages associated with prior art devices, the present invention was conceived and one of its objectives is to provide a medical device for treating swelling, inflammation, and pain.

It is another objective of the present invention to provide a medical device that is a fluid manifold that causes a fluid such as air to move across the exterior surface of a treatment site.

It is still another objective of the present invention to provide a fluid therapy device designed to move air across a treatment site via one or more channels.

It is yet another objective of the present invention to provide a fluid therapy device including at least one longitudinally extending fluid channel and one laterally extending fluid channel.

It is a further objective of the present invention to provide a fluid therapy device including at least one arcuately shaped fluid channel.

It is still a further objective of the present invention to provide a fluid therapy device with an adjustable control, whereby the amount of fluid moved by the device may be modified.

It is yet a further objective of the present invention to provide a fluid device including an enclosure sleeve for focusing the treatment system.

Various other objectives and advantages of the present invention will become apparent to those skilled in the art as a more detailed description is set forth below.

SUMMARY OF THE INVENTION

The aforesaid and other objectives are realized by providing a fluid therapy system including a negative-pressure motor positioned within a housing which has a pair of opposingly oriented sidewalls connected by a laterally extending dowel. The motor is in fluid communication with one or more treatment platforms. Each treatment platform includes one or more longitudinally oriented fluid channels and one or more laterally oriented fluid channels. The treatment platform is partially enclosed with an enclosure sleeve formed out of a pliable material to permit easy ingress and egress of the treatment member. A control panel including an adjustable structure for configuring different values of fluid movement imparted by the fluid therapy device is mounted on the exterior surface of the housing in communication with the motor.

DETAILED DESCRIPTION OF THE PREFERRED EMBODIMENT AND OPERATION OF THE INVENTION

Figure 1:
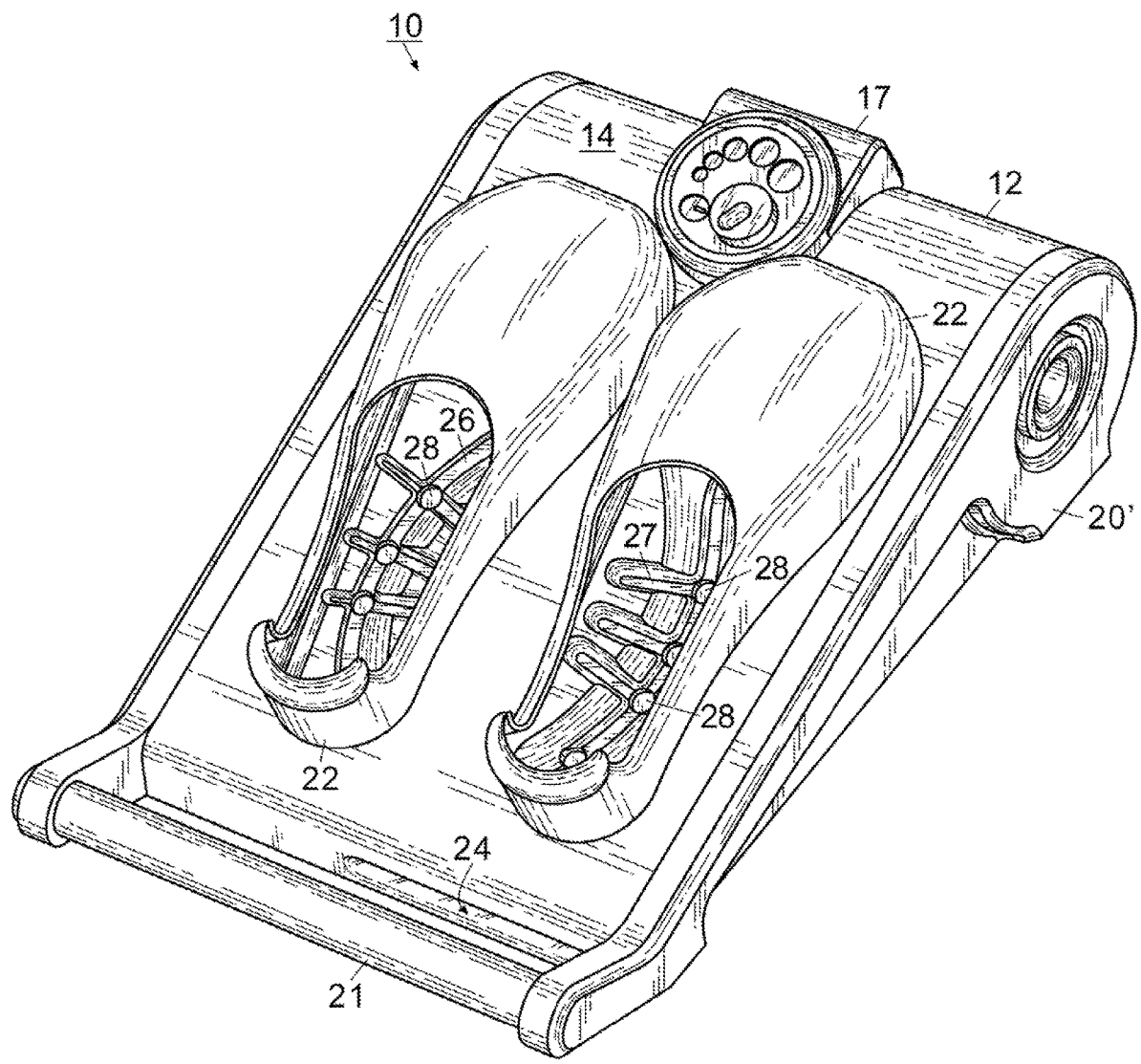
FIG. 1 shows a side perspective view of the preferred embodiment of a fluid therapy device, FIG. 2 pictures a side perspective view of the device of FIG. 1 with various elements exploded therefrom.
Figure 2:
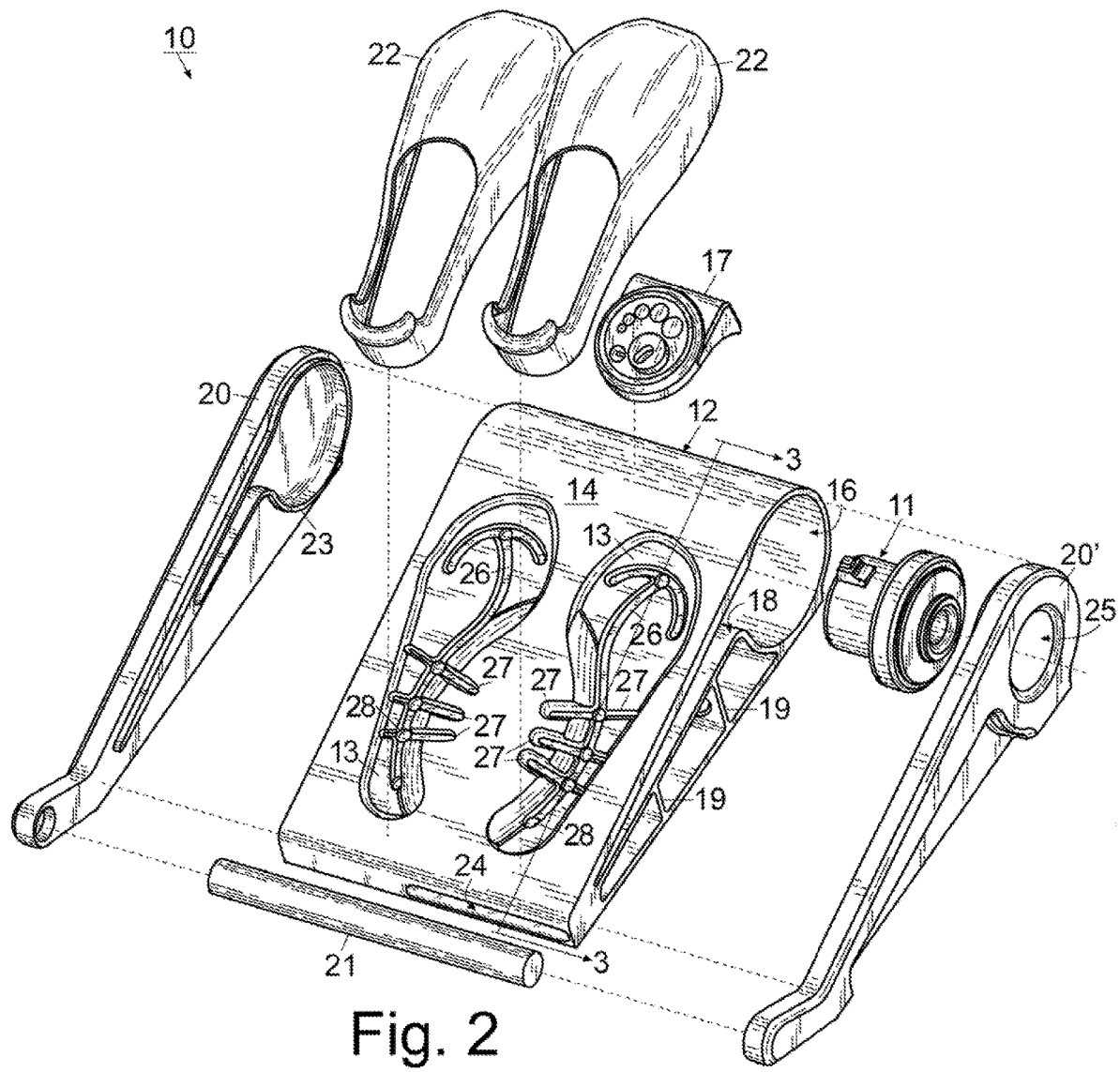
Figure 3:
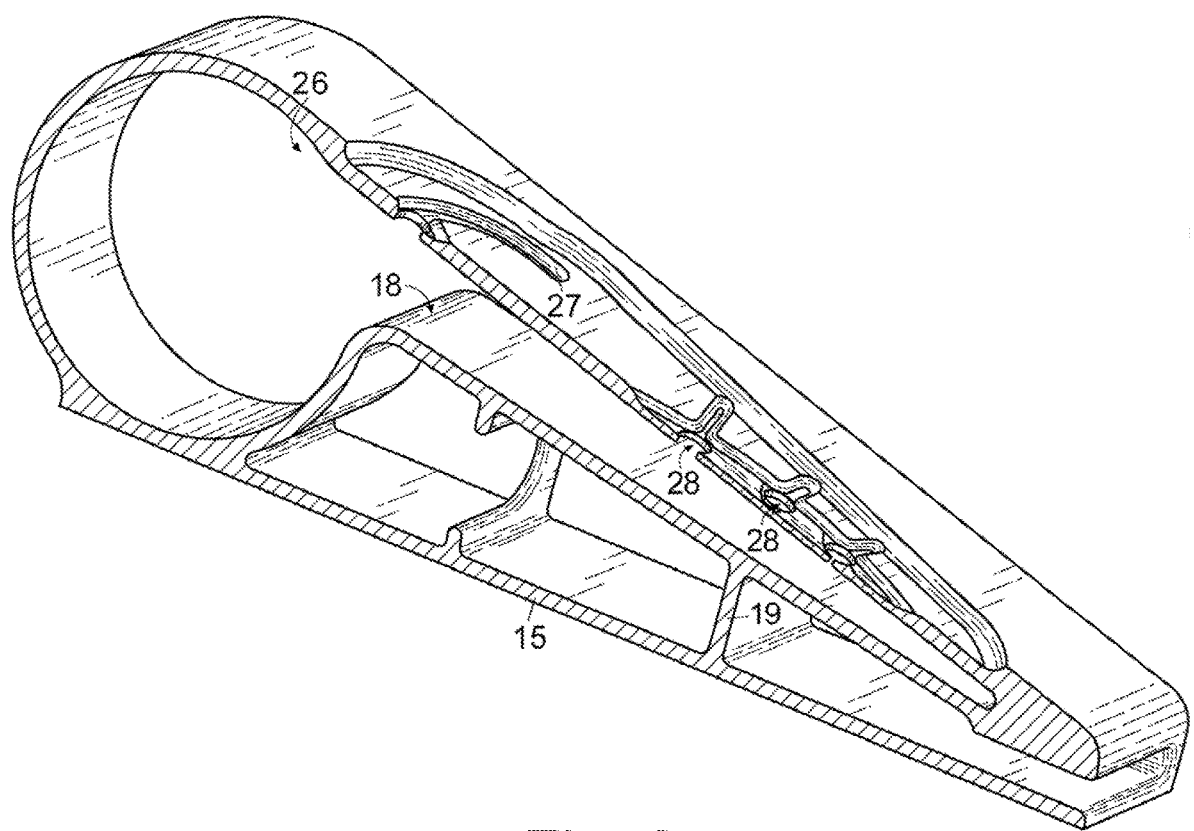
FIG. 3 depicts an elevated side view of a section of the device of FIG. 1 as seen along lines 3-3 in FIG. 2.

For a better understanding of the invention and its operation, turning now to the drawings, FIGS. 1-3 illustrate the preferred embodiment of fluid therapy device 10 including negative pressure motor 11 positioned within housing 12 and in fluid communication with one or more treatment platform(s) 13 located on an exterior surface 14 of housing 12. As demonstrated throughout the figures and following description, the preferred embodiment of fluid therapy device 10 is configured (i.e. sized and shaped) to provide treatment to one or both feet of a patient. However, it should be understood that embodiments of fluid therapy device 10 may be configured to treat other areas of the body as well, for example the wrist, the shoulder, the back, the elbow, the neck, and so on.

Housing 12 is preferably formed from a rigid material such as a polymeric material in the nature of high-density polyethylene, low-density polyethylene, polyvinyl chloride, polyethylene terephthalate, or the like. In the formation of housing 12, it is preferable to define a generally planar bottom surface 15 (see FIG. 3) and generally planar exterior top surface 14 as will de described further below. The cross-sectional shape of preferred housing 12 is that of a wedge, as a triangle produces a comfortable and aesthetically pleasing, not to mention anatomically relaxing platform on which to rest one's feet during treatment. While housing 12 can be manufactured in a various number of methods as known in the art, FIGS. 2 and 3 demonstrate that preferred housing 12 includes central aperture 16, which in the preferred embodiment is a laterally extending aperture that is sized and shaped to receive motor 11 therein. Although vacuum motor 11 is intended to be a schematic representation of the driver of negative air pressure within fluid therapy device 10 (including the connection hardware to control module 17, which is not shown), a circular or cylindrical shape defining central aperture 16 is preferred. Preferred housing 12 also includes opening 18 which in an embodiment of therapy device 10 defines a longitudinally extending opening integrally formed and in fluid communication with central aperture 16. The preferred shape of opening 18 is a carrot or cone, whereby the width of the housing walls that define opening 18 is greatest proximate central aperture 16 but narrows along the longitudinal length of opening 18 more distal from central aperture 16. This permits the flow of fluid about treatment platform 13 to remain robust, even as the distance from the negative pressure source (i.e. motor 11) increases. Housing 12 may further include one or more reinforcing ribs 19 for additional structural support of fluid therapy device 10.

An embodiment of housing 12 may include slot 24 and sidewalls 20, 20' that are positioned on laterally opposing sides of housing 12. Sidewalls 20, 20' preferably define a complementary shape to that of central aperture 16 and opening 18, and may be joined together by mutual receipt of dowel 21 at respective terminal ends. In addition to holding sidewalls 20, 20' together, dowel 21 serves as a resting perch for the user, for example as a heel stop should a specific foot size not be accommodated by sleeve 22. Dowel 21 may also serve as a convenient handle in the event fluid therapy device need be transported. Preferred sidewalls 20, 20' each define an inward extending (that is to say, towards the midline of fluid therapy device 10) ledge 23 that circumscribes the inner periphery of central aperture 16 and opening 18. In use, sidewalls 20, 20' may be inserted into central aperture 16 and opening 18 to form a tight, frictional fit to ensure that the majority of the fluid flow is in through platform(s) 13. In an embodiment of fluid therapy device 10, one of sidewalls 20, 20' may include orifice 25 (shown only on sidewall 20' in FIG. 2 for clarity) for the venting the fluid externally of fluid therapy device 10. In an alternate embodiment, orifice 25 may serve as an attachment point for an external negative pressure source, for example a conventional shop-vac hose (not shown).

One or more treatment platforms 13 are positioned on the exterior surface 14 of housing 12. It should be understood that while platforms 13 are described as separate structures relative to housing 12, nothing in this description should preclude the formation of platforms integrated into the surface of housing 12. In view of modern molding techniques of polymeric materials, such integration may be preferred. Each platform 13 may define a shape that generally corresponds to the site of treatment, so in the preferred embodiment platforms 13 generally define the shape of the human foot. Although not shown for clarity, platforms 13 may include accessory features such as cushioned pads formed from encased gel, foam, or the like. Each platform 13 includes at least one fluid channel 26 that is longitudinally extending relative to platform 13. While linear channels are contemplated within the scope of fluid therapy device 10, enhanced therapeutic results are achieved when channel 26 defines a more sinuous nature due to the more accurate anatomical connection with the therapy site. Similarly, at least one, but preferably a plurality of fluid conduits 27 extend laterally relative to platform 13. Like channel 26, arcuate embodiments of conduits 27 may be preferred, as the ergonomic shape of the foot may be better serviced in this regard. As demonstrated in FIGS. 2 and 3, conduits 27 may be positioned in various positions along platform 13 to maximize the therapeutic impact of fluid movement incurred via motor 11. For example, one conduit 27 may be located in a more fore position of platform 13, with the intent to service the toe region, while one or more conduits 27 may be positioned more aft of platform 13, with the understanding that these would service the arch and heel portions of the foot.

In the case of channels 26 and conduits 27, the intersection point of the two bodies forms hole 28 that is in fluid communication with either central aperture 16, opening 18, or both. Preferred holes 28 are circular in shape and define a sufficient diameter to match the width of both the channel 26 and conduit 27 whose intersection define it. These holes 28 facilitate the movement of fluid past the treatment area, into channels 26 or conduits 27, and into central aperture 16 or opening 18, producing the air flow that cools the surface of inflamed tissue, decreases circulation, and otherwise works with the parasympathetic nervous system to reduce inflammation, and therefore pain in a given region. The specific duration and fluid velocity necessary to generate this response may vary between users, which is why control module 17 allows the user to selectively change the operation of motor 11. In the preferred embodiment, control module 17 is mounted on exterior surface 14 with a plurality of predetermined selectable settings. The user need only rotate an indicator to the desired setting to engage fluid therapy device 10, for example high, medium, and low fluid velocity. While numerous variables exist with respect to desired outcomes associated with the use of fluid therapy device 10, it has been determined that air flow should define a velocity in excess of 180 miles per hour (80.47 meters per second), and more preferably about 200 hundred miles per hour (89.41 meters per second) to achieve the desired results described above. This fluid flow is preferably generated at between 61 inHg (approximately 30 psi) and 102 inHg (approximately 50 psi), and most preferably at about 93 inHg (approximately 45 psi). These are not considered general ranges, as the temperature decrease measured at the treatment surface need be sufficient to reduce the swelling and subsequent pain as described above, and such temperature changes are not possible without significant fluid velocity.

Fluid therapy device 10 is not a conventional vacuum therapy device, in the sense that it does not require the user to engage the surface of the treatment area with a closed system, negative-pressure stimulus. Quite the contrary, placement of the treatment area on platform 13 should not obscure in a meaningful way holes 28, as to do so would prevent the air flow and subsequent healing effects described above. Rather, the treatment article should reside in close proximity, but not mechanically or fluidly contact holes 28. However, the system may be aided by efficiency, for example sleeves 22 which reduce the amount of fluid needed to be moved around the treatment area. For example, by placing a foot on platform 13 within sleeve 22, a significantly greater impact of moving fluid as a function of a stimulus on the treatment area is realized compared to the same action taken without sleeve 22. Although it can take many shapes, sleeve 22 is preferably formed from a deformable material such as neoprene (i.e. polychloroprene) that permits a degree of flexion to accommodate a variety of treatment area sizes. Sleeve 22 is open on the bottom, but otherwise generally conforms to the size and shape of platform 13. While demonstrated as separated from housing 12 in FIG. 2, is should be understood that sleeves 22 are affixed about the periphery of respective platforms 13 at exterior surface 14 of housing 12 by mechanical fasteners, adhesives, or other robust attachment methods so as to prevent the disassociation of sleeve 22 from fluid therapy device 10, as well as providing the efficiency improvement described above. Further, it is expected that fluid flow will be sufficient with the foot of the user inserted into sleeve 22 (not shown) such that the flow of fluid into fluid therapy device 10 will be enough for its intended purpose. However, in the event these anticipated gapped openings (not shown) are not sufficient to permit an appropriate amount of fluid to flow past the desired treatment area, an embodiment of fluid therapy device 10 may include one or more accessory openings, for example positioned proximate the toe portion of sleeve 22 or formed proximate the ankle portion of sleeve 22, to further increase the flow of fluid into fluid therapy device 10.

The illustrations and examples provided herein are for explanatory purposes and are not intended to limit the scope of the appended claims.

I claim:

1. A fluid therapy device comprising:
   a reduced pressure source operable to create a reduced pressure environment,
   a housing containing the reduced pressure source, and
   at least one treatment platform carried by the housing and in fluid communication with the reduced pressure source, wherein the at least one treatment platform includes a longitudinally extending channel and a laterally extending conduit in fluid communication with the reduced pressure source, wherein the longitudinally extending channel and the laterally extending conduit intersect at an intersection which defines a hole.

2. The fluid therapy device of claim 1 further comprising an adjustable control module in communication with the reduced pressure source.

3. The fluid therapy device of claim 1 further comprising at least one sleeve affixed about the periphery of the at least one treatment platform.

4. The fluid therapy device of claim 3 wherein the at least one sleeve is made from neoprene.

5. The fluid therapy device of claim 1 wherein the longitudinally extending channel defines a sinuous shape.

6. The fluid therapy device of claim 1 wherein the laterally extending conduit defines an arcuate shape.

7. The fluid therapy device of claim 5 wherein the laterally extending conduit defines an arcuate shape.

8. The fluid therapy device of claim 1 wherein the at least treatment platform further includes additional three lateral extending conduits.

9. The fluid therapy device of claim 8 wherein a first laterally extending conduit of the lateral extending conduits is positioned fore on the at least one treatment platform relative to the three other lateral extending conduits.

10. The fluid therapy device of claim 9 wherein second, third and fourth conduits of the lateral extending conduits are positioned aft on the at least one treatment platform relative to the first lateral extending conduit.

11. A fluid therapy device comprising:
    a reduced pressure source operable to create a reduced pressure environment,
    a housing containing the reduced pressure source, the housing carrying an adjustable control module in communication with the reduced pressure source, the housing comprising an internal central aperture sized and shaped to receive the reduced pressure source and an internal opening in fluid communication with the internal central aperture, and
    at least one treatment platform carried by the housing and in fluid communication with the reduced pressure source, wherein the at least one treatment platform includes a longitudinally extending channel and a laterally extending conduit in fluid communication with the reduced pressure source.

12. The fluid therapy device of claim 11 comprising a pair of side walls, each of the side walls attached at opposing lateral ends of the housing respectively.

13. The fluid therapy device of claim 11 wherein a pair of side walls each having a complementary shape corresponding to a shape defined by the internal central aperture and the internal opening.

14. The fluid therapy device of claim 13 wherein the pair of side walls each having a ledge, the ledge extending to circumscribe an inner periphery of the complimentary shape corresponding to the shape defined by the internal central aperture and the internal opening.

15. The fluid therapy device of claim 11 wherein the longitudinally extending channel defines a sinuous shape, and wherein the laterally extending conduit defines an arcuate shape.

* * * * *